United States Patent
Heckendorn et al.

(10) Patent No.: US 8,926,950 B2
(45) Date of Patent: Jan. 6, 2015

(54) ORAL CARE COMPOSITION COMPRISING STANNOUS AND NITRATE IONS

(75) Inventors: René Heckendorn, Basel (CH); Alan Ceresa, Allschwill (CH); Elisabeth Scherrer, Hofstetten (CH)

(73) Assignee: GABA International Holding AG (CH)

( * ) Notice: Subject to any disclaimer, the term of this patent is extended or adjusted under 35 U.S.C. 154(b) by 0 days.

(21) Appl. No.: 13/639,974

(22) PCT Filed: Apr. 7, 2011

(86) PCT No.: PCT/EP2011/055458
§ 371 (c)(1),
(2), (4) Date: Oct. 8, 2012

(87) PCT Pub. No.: WO2011/124659
PCT Pub. Date: Oct. 13, 2011

(65) Prior Publication Data
US 2013/0039867 A1   Feb. 14, 2013

(30) Foreign Application Priority Data
Apr. 7, 2010   (EP) .................................... 10159201

(51) Int. Cl.
*A61Q 11/00* (2006.01)
*A61K 8/19* (2006.01)

(52) U.S. Cl.
CPC . *A61K 8/19* (2013.01); *A61Q 11/00* (2013.01); *A61K 2800/52* (2013.01); *A61K 2800/59* (2013.01); *A61K 2800/87* (2013.01)
USPC ............................................... 424/49; 424/52

(58) Field of Classification Search
CPC ........................ A61Q 11/00; A61K 2300/00
USPC .................................................. 424/49, 52
See application file for complete search history.

(56) References Cited

U.S. PATENT DOCUMENTS

| | | | |
|---|---|---|---|
| 3,083,143 | A | 3/1963 | Schmid et al. |
| 5,004,597 | A | 4/1991 | Majeti et al. |
| 5,603,922 | A | 2/1997 | Winston et al. |
| 5,693,314 | A | 12/1997 | Campbell et al. |
| 6,280,708 | B1 * | 8/2001 | Ryles et al. ............. 424/53 |
| 2007/0025928 | A1 | 2/2007 | Glandorf et al. |

FOREIGN PATENT DOCUMENTS

| | | |
|---|---|---|
| CN | 101511327 | 8/2009 |
| EP | 0026539 | 4/1981 |
| EP | 0514966 | 11/1992 |
| EP | 2057978 | 5/2009 |
| EP | 2281543 | 2/2011 |
| EP | 2281544 | 2/2011 |
| GB | 1239748 | 7/1971 |
| RU | 2270668 | 3/2004 |
| WO | WO 98/02135 | 1/1998 |
| WO | WO 98/22427 | 5/1998 |
| WO | WO 99/53893 | 10/1999 |
| WO | WO 2007/020939 | 2/2007 |
| WO | WO 2008/041055 | 4/2008 |
| WO | WO 2009/130319 | 10/2009 |
| WO | WO 2011/016982 | 2/2011 |
| WO | WO 2011/016983 | 2/2011 |

OTHER PUBLICATIONS

Database GNPD Mintel, 2000, Colgate-Palmolive "Toothpaste Maximum Strength Sensitive plus Whitening," AN: 10076005.
Donaldson et al., 1961, "Basic Tin(II) Nitrate," J. Chem. Soc. pp. 1996-2000.
Farrow et al., 1970, "The Nitrate Detinning Reaction in Model Systems," J. Food Science 35:818-822.
Hamdan, 2010, "Sn(II) Selective 2-Amino-1,4-Naphthoquinone Derived Poly(Vinyl Chloride) Membrane Sensors," Int. J. Electrochem. Sci. 5:215-231.
International Search Report and Written Opinion in International Application No. PCT/EP11/055458, mailed Sep. 15, 2011.
National Research Council (US) Committee on Dental Health, 1952, "A Survey of the Literature of Dental Caries," National Academy of Sciences pp. 402-404.
Robertson, 2006, "Nitrates," Food Packaging: Principles and Practice, 2nd ed., CPC Press, Hope Island, Australia, p. 151.

\* cited by examiner

*Primary Examiner* — Frederick Krass
*Assistant Examiner* — Tracy Liu
(74) *Attorney, Agent, or Firm* — Rena Patel

(57) ABSTRACT

An oral care composition comprising a) an aqueous phase; b) stannous ions solvated in the aqueous phase; c) nitrates solvated in the aqueous phase; wherein the total content of said nitrates is such that the molar amount of nitrogen in the aqueous phase, measurable as nitrate, is less than 2 times the molar amount of solvated stannous ions; and d) a flavor substance, which is preferably solvated, dispersed or emulgated in the aqueous phase. Disclosed are also containers containing the composition; and processes and uses for stabilizing stannous ions against oxidation, using nitrates.

15 Claims, No Drawings

ORAL CARE COMPOSITION COMPRISING STANNOUS AND NITRATE IONS

CROSS-REFERENCE TO RELATED APPLICATIONS

The present application is a national stage entry under 35 U.S.C. §371 of Inernational Patent Application No. PCT/EP2011/055458, filed Apr. 7,2011, which claims the benefit of European Patent Application No. 10159201.2, filed Apr. 7, 2010, the entireties of which are hereby incorporated by reference.

FIELD OF THE INVENTION

The present invention relates to the field of oral care compositions, in particular mouthrinses, comprising stannous ions.

Stannous ions have been used in the field of oral care compositions for decades. Originally the reason for having stannous ions in an oral composition was because fluoride was added to them in the form of stannous fluoride. Other reasons for having stannous ions in their own right in oral care compositions are their desensibilising, caries-protective and demineralization-protective effect.

The addition of stannous ions to oral care compositions suffers from the drawback that stannous ions (divalent) are susceptible to oxydation by atmospheric oxygen, particularly in the mainly aqueous media found in these compositions. The oxidation gives stannic ions (tetravalent) which extensively hydrolyze in the aqueous medium to form insoluble hydroxo or oxide species which lead to precipitates and turbidity. This is particularly unwanted for oral care compositions in the form of mouthwashes or mouthrinses, which are supposed to be clear, sediment-free solutions and which with the formation of such precipitates or turbidity become unacceptable for the consumer. Stannic ions, to the extent that they remain solubilized in the composition, have lower efficacy than stannous ions.

While it may be possible to package the oral care composition under inert gas such as nitrogen or under vacuum, such inert gas atmosphere or vacuum ceases to exist once the package is opened by the consumer. Oral care compositions containing stannous ions thus need some stabilisation system that protects stannous ions against oxidation after opening of the package and during the usage time of the composition, which is typically several weeks, such as three weeks.

PRIOR ART

U.S. Pat. No. 5,004,597 A discloses that in oral care compositions stannous ions lost by oxidation by stannous ions can be replaced from a stannous gluconate reservoir.

EP 0 026 539 A discloses the stabilisation of stannous ions in aqueous media, such as in mouthrinses, by amine hydrofluorides (amine fluorides) such as OLAFLUR.

J. Chem. Soc. pp. 1996-2000 (1961) mentions that "dilute solutions of tin(II) nitrate are reasonably stable". This refers to an aqueous solution containing only tin(II) nitrate and wherein the molar ratio of nitrate ions to stannous ions is exactly 2:1.

U.S. Pat. No. 5,693,314 A and WO 99/53893 A disclose two-component compositions, one component containing stannous salt and the other component containing desensibilising amounts of potassium nitrate. The two components are to be mixed before use. U.S. Pat. No. 5,693,314 A also discloses a comparative toothpaste containing both potassium nitrate and stannous fluoride. Since in the dual component compositions of U.S. Pat. No. 5,693,314 A and WO 99/53893 A the nitrate ion in the one component was present in a large molar excess over the stannous ion in the other component, i.e. the molar ratio of nitrate ions to stannous ions was much larger than 2:1, the two components, upon mixing in a reasonable ratio such as about 1:1 (see in particular WO 99/53893, page 8, lines 31-32 and page 10, lines 15-19), gave a composition again having a large excess of nitrate over stannous ions. The said comparative toothpaste of U.S. Pat. No. 5,693,314 A contained a molar ratio of nitrate ions (ex potassium nitrate) to stannous ions (ex stannous fluoride), as calculated from the indicated weights, of 19.4:1. U.S. Pat. No. 5,693,314 A states on column 2, lines 17-20 that "prolonged contact between stannous ion and nitrate ion in a single dentifrice results in a reaction of these ions causing a conversion of $NO_3$ into potentially toxic materials".

U.S. Pat. No. 5,603,922 A discloses one or two component remineralisation compositions. These contain a calcium salt (which may be the nitrate) and a salt of another divalent cation, which may, but need not be stannous ion; the salt itself, if a stannous ion salt, may be the chloride or, nitrate. In example 9 part A it discloses a formulation containing a molar ratio of nitrate ions (ex calcium nitrate) to stannous ions (ex stannous chloride), as calculated from the indicated weights, of 332.7:1. In example 12 part A it discloses a formulation containing a molar ratio of nitrate ions (ex calcium nitrate) to stannous ions (ex stannous chloride), as calculated from the indicated weights, of 464.5:1.

The present invention seeks to provide stannous ion-containing oral care composition with improved stannous ion stability against oxidation.

SUMMARY OF THE INVENTION

The object set is solved by an oral care composition comprising a) an aqueous phase; b) stannous ions solvated in the aqueous phase; c) nitrates solvated in the aqueous phase; wherein the total content of said nitrates is such that the molar amount of nitrogen in the aqueous phase, measurable as nitrate, is less than 2 times the molar amount of solvated stannous ions; and d) a flavour substance.

Other aspects of the invention and preferred embodiments of all aspects of the invention are as in the claims.

It was unexpectedly found that when nitrates are combined in an aqueous solution with stannous ions in a molar ratio of nitrogen, measurable as free nitrate, to stannous ions which is less than 2:1, then, firstly, the nitrates do not noticeably react with stannous ions. It was furthermore unexpectedly found that in this case the stannous ions are also stabilized against oxidation by atmospheric oxygen.

DETAILED DESCRIPTION OF THE INVENTION

The oral care composition of the invention may be any such formulation, e.g. a toothpaste, dental gel, touch solution, mouthrinse and so on. Preferably it is a mouthrinse.

The oral care compositions of the invention contain an aqueous phase. They are thus synonymously also referred to as "aqueous compositions". By "aqueous phase" is understood that this phase contains typically 30% to 99%, preferably 40% to 95% by weight, based on the liquid phase, of water. The aqueous phase may be liquid, meaning it has a dynamic viscosity at room temperature of not more than 1000 mPa·s. The aqueous phase may also be in the form of a gel or syrup, which may be accomplished by adding water-soluble gelling or thickening agents acceptable for an oral care formulation, or by adding co-solvents of higher viscosity than water, such as glycerol or propylene glycol. Not as part of the aqueous phase are understood any non-dissolved solids, such as abrasives, that could be suspended or dispersed in or mixed with the aqueous phase and that could be separated from the overall oral care formulation by physical solid-liquid separation operations such as filtration, sedimentation, flotation or centrifugation, optionally after diluting the oral care formulation twenty-fold with water. The aqueous phase may also comprise certain amounts, such as 1 to 15 vol %, based on the aqueous phase, of ethanol. Preferably the aqueous phase is a liquid with the abovementioned dynamic viscosity. The pH of the aqueous phase is typically in the range of 3.0 to 6.0, preferably in the range of 4.0 to 6.0 and most preferably in the range of 4.0 to 5.0.

The oral care compositions of the invention comprise "stannous ions solvated in the aqueous phase". This term is intended to encompass all ionic tin species in the formal oxidation state +II in the liquid phase. Examples of such tin species are hydrated stannous ions, soluble ionic or nonionic complexes of stannous ions and ionic hydroxo complexes of stannous ions. The amount of solvated stannous ions is typically 100 to 2500 ppm, preferably 150 to 1000 ppm, more preferably 150 to 500 ppm of solvated stannous ions, based on the aqueous phase. The content of solvated stannous ions may be determined potentiometrically (see example 10). The solvated stannous ions may be derived from a pharmaceutically acceptable stannous salt. Examples are stannous chloride, stannous fluoride, stannous hydroxide, stannous sulfate, with stannous fluoride being preferred. What has been designated in the above mentioned prior art as "stannous nitrate" is not suited as the sole stannous ion source and simultaneously sole nitrate ion source since it would give in the oral composition a molar ratio nitrogen, measurable as nitrate, to stannous ions of 2:1, which is not according to the invention.

The oral care compositions of the invention comprise in their aqueous phase solvated nitrates. The term "nitrates" encompasses all water-soluble inorganic species containing one or more $NO_3^-$ moieties each (coordinated to a cation or as counter anion(s)). Examples of nitrates are nitrato complexes of metal cations present in the aqueous phase of the oral composition, such as of stannous ions, solvated nitrate counter anions and undissociated nitric acid. The solvated nitrate anions are assumed to be nitrate anion solvated by water molecules and having essentially non-complexing cations, such as of sodium, potassium or the cations of amine fluorides cation (see below) as counter ions. Since all these nitrates will normally be in thermodynamic equilibrium with each other it is not possible to determine the molar amounts of each of these nitrates individually. The common feature of all these nitrates is, however, that upon alkalinisation they are converted to solvated nitrate anions by deprotonation of any nitric acid and/or by precipitation of the metal cations from any nitrato complexes as insoluble hydroxides or oxides. Essential for the purposes of the invention is that the total content of all these nitrates solvated in the aqueous phase of the oral composition, i.e. the molar amount of nitrogen contained in them and being measurable after alkalinisation (but without any other or further chemical conversion such as oxidation) as nitrate anions (see example 11), is less than 2 times the molar amount of stannous ions solvated in the aqueous phase. If the nitrates solvated in the aqueous phase are assumed to contain only one $NO_3^-$ moiety each (coordinated or as anion), then the molar amount of these $NO_3^-$ moieties, and thus the molar amount of solvated nitrates themselves, is equal to said molar amount of nitrogen. In this case the said ratio of molar amount of nitrogen measurable as nitrate to solvated stannous ions is also referred to for short as "molar ratio of nitrates to stannous ions".

Said nitrates may be obtained by adding sodium or potassium nitrate to the aqueous phase of the composition. The "stannous nitrate" of the prior art may also be used, but then in combination with another stannous salt to give a molar ratio of nitrogen, measurable as nitrate, to solvated stannous ions of less than 2:1 as is in acordance with the instant invention. Nitrate ions and stannous ions in a molar ratio of about 0.66:1 may be simultaneously added using the crystalline so-called "basic" stannous nitrate (believed to have the formula $Sn_3(OH)_4(NO_3)_2$), particularly if the aqueous phase to which it is added has been acidified beforehand with a little amount of acid to prevent hydrolysis to hydrous tin(II)oxide. Such composition could then be made free of both sodium and potassium. This salt can be prepared in crystalline form and is stable at room temperature; although at higher temperatures it may detonate. Nitrates may also be generated in the aqueous phase of the composition by adding silver nitrate to an aqueous phase in which stannous ions have been solvated by adding stannous chloride. In this process any added silver ions can be quantitatively precipitated as silver chloride, as long as noticeable amounts of chloride are present in the aqueous phase. The remaining of noticeable amounts of chloride in this process is tantamount to having a noticeable amount of stannous chloride not yet methathesized to stannous nitrate, which in turn is in accordance with the requirement of the invention that the molar amount of nitrogen, measurable as nitrate, be less than 2 times the molar amount of stannous ions. For short this means that as long as silver chloride can be precipitated upon adding silver nitrate, then the molar amount of amount of nitrogen measurable as nitrate, is still lower than 2 times the molar amount of stannous ions, in accordance with the invention.

The oral care compositions of the invention also comprise a flavour substance. This flavour substance is preferably solvated, dispersed or emulgated in the aqueous phase. Exemplary sub-classes of the flavour substance that may be comprised in the oral care composition of the invention are:

i) Ethereal oils or essences obtained from vegetable sources such as basil oil, bitter almond oil, camphor oil, citronella oil, citrus oils, apple, eucalyptus or spearmint essenc, Eucalyptus citriodora oil, eucalyptus oil, aniseed oil, anethol, camomile oil, spearmint oil, lime oil, mandarin oil, clove oil, orange oil, citrus oil, peppermint oil, spearmint oil, sage oil, thyme oil, vanillin, wintergreen oils, cinnamon oil or cinnamon bark oil;

ii) natural or synthetic compounds producing a "warm" or "hot" sensation. Examples thereof include capsaicin, dihydrocapsaicin, gingerol, paradol, sho gaol, piperine, paprika powder, chilli pepper powder, extracts from paprika, extracts from pepper; extracts from chilli pepper; extracts from ginger roots, extracts from Aframomum melgueta, extracts from Spilanthes acmella, extracts from Kaempferia galanga, extracts from Alpinia galanga, carboxylic acid N-vanillylamides, in particular nonanoic acid N-vanillylamide, 2-nonenoic acid amides, in particular 2-nonenoic acid N-isobutylamide and 2-nonenoic acid N-4-hydroxy-3-methoxyphenylamide, alkyl ethers of 4-hydroxy-3-methoxybenzyl alcohol, in particular 4-hydroxy-3-methoxybenzyl n-butyl ether, alkyl ethers of 3-hydroxy-4-methoxybenzyl alcohol, alkyl ethers of 3,4-dimethoxybenzyl alcohol, alkyl ethers of 3-ethoxy-4-hydroxybenzyl alcohol, alkyl ethers of 3,4-methylenedioxybenzyl alcohol, (4-hydroxy-3-methoxyphenyl)acetic acid amides, in particular (4-hydroxy-3-methoxyphenyl)acetic acid N-n-octylamide, nicotinaldehyde, methyl nicotinate, propyl nicotinate, 2-butoxyethyl nicotinate, benzyl nicotinate and 1-acetoxychavicol;

iii) natural or synthetic compounds having a "cooling" effect. Examples thereof are primarily 1-menthol, but also menthone glycerol acetal, menthyl lactate, substituted menthyl-3-carboxylic acid amides (e.g. menthyl-3-carboxylic acid N-ethylamide), 2-isopropyl-N,2,3-trimethylbutanamide, substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, menthyl hydroxycarboxylic acid esters (e.g. menthyl 3-hydroxybutyrate), monomenthyl succinate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl 3,6-di- and tri-oxaalkanoates, 3-menthyl methoxyacetate, icillin and 1-menthyl methyl ether.

The oral care composition of the invention may comprise one or several flavour substances such as those outlined above. The type and amount of the flavour substance(s) depends on the intended taste to be achieved for the oral care compositions. Exemplary total amounts of flavour substances are 0.01% to 0.5%, preferably 0.03% to 0.3% by weight, based on the oral care composition.

The flavour substance or flavour substances may be water-soluble, in which case simple dissolution will serve to solvate these substances in the aqueous phase. Alternatively they may be weakly water-soluble or water-insoluble, in which case they may be solubilized using an appropriate co-solvent, such as the abovementioned 1 to 15 vol %, based on the aqueous phase, of ethanol. They may also be solubilized, dispersed or emulgated using customary surfactants, as is known in the art of oral care compositions. Preferred subclasses of surfactants are non-ionic (such as hydrogenated castor oil, cationic (such as acid addition salts of fatty amines or amine fluoride) and zwitterionic surfactants (such as cocamidopropyl betaine).

Industrial fragrance companies, such as Symrise, Mane Fils, Givaudan, Firmenich or International Fragrances provide ready-to-use mixtures of flavour substances that can be used in the oral care compositions.

The oral care composition of the invention may preferably also comprise fluoride. The fluoride content of the oral care compositions is typically from 50 to 2000 ppm, based on the composition, preferably from 100 to 1000 ppm. Preferably the fluoride is dissolved in the liquid phase of the composition. The fluoride content of the oral care composition may be determined potentiometrically using a fluoride-selective electrode (see example 12). The fluoride may be added to the oral care composition in the form of any fluoride ion source customarily employed in oral care compositions, e.g. as stannous fluoride, sodium fluoride or amine fluoride. The latter is preferred; examples for utilizable amine hydrofluorides are those described in U.S. Pat. No. 3,083,143 A, WO 98/22427 A and WO 2009/130319 A, these three publications being included in their entirety by reference. Particularly preferred is the amine hydrofluoride made by adding mol equivalents of hydrofluoric acid to N,N'N'-tris(2-hydroxyethyl)-N-octadecenyl-1,3-diaminopropane free base, which amine fluoride is known as Olaflur.

The oral care composition of the invention may contain colourants accepted for an oral care composition. It is, however, preferably essentially free of dyes having singlet oxygen sensitizer properties, examples of such dyes being triaryl methane dyes and their derivatives, in particular Patent Blue V (E131; sodium or calcium salt of [4-(α-(4-diethylaminophenyl)-5-hydroxy-2,4-disulfophenyl-methylidene)-2,5-cyclohexadien-1-ylidene]diethylammonium hydroxide, inner salt). By "essentially free" is understood that the oral composition comprises less than 0.05% by weight, preferably less than 0.001% by weight in total of such singlet sensitizing dyes. "Essentially free" may mean that there are no such dyes present at all, or that there is a minimum, non-zero amount of such dyes present, that minimum amount being typically 0.00001% by weight.

The oral care formulation of the invention may also comprise non-cariogenic sweetening sugar alcohols. Examples thereof are erythritol, threitol, arabitol, xylitol, sorbitol, ribitol and maltitol. A typical range of total content for these sugar al-cohols is 5% to 45% by weight, based on the oral care composition. These sugar alcohols are preferably dissolved in the liquid phase.

The oral care composition of the invention may be adjusted to a physiologically acceptable pH value in the range of 3.0 to about 6.0, preferably about 4.0 to about 6.0, more preferably about 4.0 to about 5.0. This may be achieved using customary buffering systems such as dihydrogen citrate/monohydrogen citrate; lactic acid/lactate, or gluconic acid/gluconate buffers. The exact desired pH of the oral care composition may be achieved by adjusted by adding acid (such as hydrochloric acid) or base (such as sodium hydroxide).

The compositions of the invention, when they are mouthrinses, are clear solutions essentially, preferably completely free of suspended or sedimented solids or from turbidity.

Further optional components in all types of oral care composition of the invention may be for instance:

Sweeteners, in particular artificial sweeteners such as saccharin, acesulfam, neotam, cyclamate or sucralose; natural high-intensity sweeteners such as thaumatin, stevioside or glycyrrhizin; or sugar alcohols different from the $C_{(3-5)}$ sugar alcohol, such as sorbitol, xylitol, maltitol or mannitol. These may be present in amounts of 0% to 0.2%, preferably 0.005% to 0.1% by weight, based on the composition.

Antibacterials and/or preservatives, such as chlorhexidine, triclosan, quaternary ammonium compounds (such as benzalkonium chloride) or parabens (such as methyl or propyl paraben). The amount of antimicrobial agent in the oral care composition is typically from 0 to about 0.5%, preferably 0.05 to 0.1% by weight, based on the oral care composition.

Emulsifiers or solubilisers, mainly in connection with above-mentioned flavour substance(s) and/or antibacterials, which often are of low solubility in aqueous media. Examples of such emulsifiers are neutral surfactants (such as polyoxyethylene hydrogenated castor oil or fatty acids of sugars), anionic surfactants (such as sodium lauryl sulfate), cationic surfactants (such as the ammonium cations of formula (I)) or zwitterionic surfactants. These surfactants or solubilisers may be present in amounts of typically 0% to 2%, preferably 0.2% to 1.5% by weight, based on the oral care composition.

Thixotropic agents, such as soluble grades of hy-droxypropylmethylcellulose, hydroxyethylcellulose or mucins, in an amount effective to impart the oral care composition a thixotropic behaviour.

Stabilisers, such as polyvinylpyrrolidone.

Further optional components for oral care compositions of the invention that have a solid phase, such as in particular toothpastes or dental gels, are abrasives, such as inorganic abrasives (e.g. silica, aluminium oxide, calcium carbonate, calcium phosphate, calcium pyrophosphate or stannous pyrophosphate) or organic abrasives (such as polyethylene, polyvinyl chloride, polystyrene, polycarbonate, copolymers from (meth)acrylates and other olefinic monomers, polyamides, urea-formaldehyde resins, melamine-formaldehyde resins, phenol-formaldehyde resins, cured, pulverised epoxy resins or polyesters).

Since it has been found that stannous ions are stabilized in aqueous solution against oxidation by solvated nitrates, it is an object of the invention to provide a such a stabilization process. The invention also concerns single-compartment containers wherein the oral care composition of the invention is stored, or is stored and then dispensed. Since stannous ions have been found to be highly stabilised against oxidation by these nitrates, it has become possible to provide long-time-storable oral care compositions (e.g. for three weeks) containing stannous ions and nitrates in one and the same component of such a container; and it has become possible to handle such oral care compositions without taking special precautions against oxygen gas. Thus, it is possible but no longer necessary to subject the composition to a degassing, in order to remove dissolved gaseous oxygen, prior to the filling into the storage container or storage and dispensing container of the invention. It is possible, but also no longer necessary to subject the ingredients for the oral care composition, such as in particular the abrasives used for a toothpaste of the invention, to a beforehand degassing. These abrasives are quite porous and have a high specific surface and may harbour appreciable amounts of gaseous oxygen or air which are difficult to remove after having added these abrasives to the toothpaste. The oral care composition of the invention, once filled into the storage container or storage and dispensing container of the invention, thus may contain some solvated oxygen gas. It is possible, but no longer necessary either to purge the storage container or storage and dispensing container of the invention with nitrogen or another inert gas, or to evacuate it, before and/or after filling the oral care composition of the invention into them. Their single compartment may be completely filled with the oral care composition of the invention. Generally however, their single compartment will not be completely full of the composition, but also comprise a gas phase. This gas phase may be, as was customary in the art, a protective gas atmosphere such as of pure nitrogen, or a vacuum. Preferably however, that gas phase is simply air.

Examples of single compartment storage containers of the invention are storage tanks, bottles, canisters or vessels in production or packaging facilities. Examples for single compartment storage and dispensing containers, containing particularly preferably a mouthrinse or touching solution of the invention, are capped bottles or vials, wherein the cap, when removed from the bottle, may simultaneously serve as a cup to take up a defined aliquot of, say, 10 ml of the oral care composition. The walls of such container may be a "multilayer" wall, meaning it consists of several layers of different materials to lower permeability for oxygen; or it may be a "monolayer" wall, consisting of only one material such as plastic. Examples for single compartment storage and dispensing containers, containing particularly preferably a toothpaste or dental gel of the invention, are squeezable tubes. All these containers are preferably closed, once they contain the composition of the invention. The closing may be, but needs not be gas-tight. The closing is preferably liquid-tight.

The invention will now be further explained by the following non-limiting examples.

EXAMPLES

Examples 1-9

Mouthrinse Formulations

In the following examples the amounts of all ingredients listed in the table are in percentages by weight, based on the overall mouthrinse.

| | Example No. | | | | | |
|---|---|---|---|---|---|---|
| | 1 | 2 | 3 | 4 | 5 | 6 |
| Added oral care actives | 0 ppm $F^-$ [Sn] 400 ppm | 0 ppm $F^-$ [Sn] 125 ppm | 0 ppm $F^-$ [Sn] 250 ppm | 256 ppm $F^-$ [Sn] 800 ppm | 500 ppm $F^-$ [Sn] 500 ppm | 300 ppm $F^-$ [Sn] 150 ppm |
| nitrate:$Sn^{2+}$ molar ratio | 1:1 | 1:1 | 1.1:1 | 1.2:1 | 0.9:1 | 1:1 |
| $SnCl_2$ dihydrate | 0.0760 | 0.0237 | 0.0475 | | | |
| $SnF_2$ | | | | 0.1056 | 0.0660 | 0.0199 |
| NaF | | | | | 0.0751 | 0.0556 |
| $NaNO_3$ | 0.0287 | 0.0090 | 0.0197 | 0.0688 | 0.0322 | 0.0107 |
| Cremophor RH 410 | | | | 1 | 0.5 | 0.2 |
| Flavour | | | | 0.44 | 0.22 | 0.14 |
| Sodium saccharin | | | | 0.06 | | 0.05 |
| Acesulfam K | | | | | 0.1 | |
| Glycerol | 30 | 35 | 30 | 30.5 | 26 | 39 |
| Deionised water | q.s. ad 100% | q.s. ad 100% | q.s. ad 100% | q.s. ad 100% | q.s. ad 100% | q.s. ad 100% |

| | Example No. | | |
|---|---|---|---|
| | 7 | 8 | 9 |
| Added actives | 250 ppm $F^-$ (125 ppm ex $SnF_2$, 125 ppm ex AmF) [Sn] 400 ppm | 250 ppm $F^-$ (125 ppm ex $SnF_2$, 125 ppm ex AmF) [Sn] 400 ppm | 250 ppm $F^-$ (125 ppm ex $SnF_2$, 125 ppm ex AmF) [Sn] 400 ppm |
| nitrate:$Sn^{2+}$ molar ratio | 1:1 | 0.8:1 | 1.3:1 |

-continued

| | | | |
|---|---|---|---|
| Olaflur | 0.1641 | 0.1641 | 0.1641 |
| SnF$_2$ | 0.0515 | 0.0515 | 0.0515 |
| KNO$_3$ | 0.0341 | 0.0256 | 0.0426 |
| PEG-40 hydrogenated castor oil | 0.25 | 0.25 | 0.25 |
| Flavour | 0.11 | 0.11 | 0.11 |
| Sodium saccharin | 0.05 | 0.05 | 0.05 |
| Xylitol | 0.85 | 0.85 | 0.85 |
| PVP | 0.30 | 0.30 | 0.30 |
| Patent Blue V | 0.0002 | 0.0002 | 0.0002 |
| Deionised water | q.s. ad 100% | q.s. ad 100% | q.s. ad 100% |

Example 10

Measurement of Molar Amount of Stannous Ions Solvated in the Aqueous Phase of an Oral Care Composition of the Invention A combined platinum electrode type 6.1204.310 of Metrohm, Switzerland, and a potentiometer Titrando 809 of Metrohm, Switzerland, are used. The calibration of the electrode is done according to the manual.

10.0000 g of the oral care composition are exactly weighed (±0.1 mg) in a 100 ml container and 40 ml water, 5 ml 32 wt % HCl and a known aliquot v (in ml) of standard 0.05 M KI$_3$ solution is added, such that iodine is added in excess of the tin in formal oxidation state +II contained in the sample (a typical value for v is 5 ml).

The electrode is immersed into the sample solution and the remaining iodine not already reduced to I$^-$ by the tin in formal oxidation state +II is titrated back with standard 0.1 M Na$_2$S$_2$O$_3$ solution to the endpoint of the titration. The used amount of Na$_2$S$_2$O$_3$ solution in ml is taken as v$_1$.

The amount of stannous ions contained in the sample, in ppm based on the oral composition, [Sn$^{+II}$], is obtained as $$[Sn^{+II}]=593.45(v-v_1).$$

If the oral composition consisted of an aqueous phase, without having any solids, then the molar amount of stannous ions solvated in the above 10.0000 g oral care composition, Sn$^{2+}_{aq}$ (in millimoles), is obtained from the above [Sn$^{+II}$] as $$Sn^{2+}_{aq}=8.425\times10^{-5}\times[Sn^{+II}].$$

Alternatively, if the oral composition contained an aqueous phase and solids, then another 10.0000 g of the oral care composition are diluted with 40.0000 g water, filtrated and the solids filtered off are dried to constant weight. The weight of these dried solids, in grams, is designated as m$_s$. The molar amount of stannous ions solvated in the aqueous phase of the above 10.0000 g oral care composition, Sn$^{2+}_{aq}$ (in millimoles), is obtained from the above [Sn$^{+II}$] as $$Sn^{2+}_{aq}=8.425\times10^{-6}\times(10-m_s)\times[Sn^{+II}].$$

Example 11

Measurement of the Content of Nitrates in Oral Care Compositions of the Invention 1.0000 g±0.1 mg of the oral care composition are exactly weighed in a container and water is added to make a total weight of 20.0000 g±0.1 mg. The determination is done by ion chromatography on a 20 microlitre sample of the supernatant solution:

Instrument: Dionex IC 25 Ion Chromatograph with autosampler AS 50 with an eluent generator EG 40 with a EluGen Cartridge KOH.

Column: Dionex Ion Pac AS 14, i.d. 4 mm, length 250 mm, with pre-column Ion Pac AG14A, i.d. 4 mm, length 50 mm.

Suppressing system: Dionex Anion Self Regenerating Suppressor, (ASRS-ULTRA II i.d. 4 mm).

Eluent: 40 mM potassium hydroxide solution. This alkaline eluent converts, upon contact with the sample, all nitrates contained therein into nitrate anions.

Flow rate: 0.9 ml per minute.

The molar amount of nitrate anions {NO$_3^-$} derived from the 20 microlitre sample is evaluated from the area of the nitrate peak in the ion chromatogram of the sample, using a calibration curve of molar amount of nitrate vs. peak area. This calibration curve is prepared by measuring under the same ion chromatographic conditions 20 microlitre aliquots of solutions containing known, but variable molar amounts of potassium nitrate in an useful range.

If the oral care composition consists only of an aqueous phase, and {NO$_3^-$} is given in micromoles, then the molar amount of nitrogen in the above 1.0000 g oral care composition, measurable as nitrate, which is designated as {N} (in millimoles), is directly equal to {NO$_3^-$}.

Alternatively, if the oral composition contained an liquid (aqueous) phase and solids (e.g. abrasives), then another 1.0000 g of the oral care composition are diluted to 20.0000 g with water, filtrated and the solids filtered off are dried to constant weight. The weight of these dried solids, in grams, is designated as m$_s$. The molar amount of nitrogen measurable as nitrate (in millimoles) in the aqueous phase of the above 1.0000 g oral care composition, which is designated as {N} (in millimoles), is obtained from above {NO$_3^-$} as $$\{N\}=(1-m_s)\times\{NO_3^-\}.$$

If all solvated nitrates present in the aqueous phase are assumed to contain one NO$_3^-$ moiety each (coordinated or as anion), then the molar amount of these NO$_3^-$ moieties, and thus the molar amount of nitrates themselves, is equal to {N}.

Example 12

Potentiometric Fluoride Determination in Oral Care Composition of the Invention

A fluoride-selective electrode type 6.0502.150 of Metrohm, Switzerland, a pH/Ion-meter 692, Metrohm, Switzerland and an Ag/AgCl reference electrode type 6.0750.100, Metrohm, Switzerland are used.

A total ionic strength adjusted buffer (TISAB) is required and made as follows: A solution of 160 mg NaOH in 2 litres of water is prepared (solution 1); 25 g 1,2-diaminocyclohexane-N,N,N',N'-tetraacetic acid, 290 g NaCl and 285 ml glacial acetic acid are dissolved in 2 litres of water (solution 2); then solutions 1 and 2 are mixed and filled up to 5 litres with water.

The calibration of the fluoride-selective electrode is performed according to the manual of the pH/Ion-meter.

1.0000 g±0.1 mg of the oral care composition are exactly weighed in a 50 ml plastic container and filled up with water to a weight of 20.0000 g±0.1 mg, and 20 ml of above mentioned TISAB buffer are added. The fluoride-selective electrode and the reference electrode are immersed into the sample and the potential is read off after 5 minutes, according to the manual of the pH/Ion-meter. The fluoride concentration in ppm is calculated by multiplying the measured response-value by 40 (the total dilution factor from the oral care composition to the measured sample), and dividing by the weight of the oral care composition sample in g.

Example 13

Stability of Stannous Ions without Nitrate and in Presence of 1 Molar Equivalent and 2 Molar Equivalents of Nitrate Three aqueous solutions of 211 mg $SnF_2$ in 400 ml distilled water were prepared. These solutions thus contained an initial 400 ppm of solvated $Sn^{2+}$. The first solution was without potassium nitrate; to the second were added 136 mg potassium nitrate (=1 molar equivalent with respect to stannous ions) and to the third were added 272 mg potassium nitrate (=2 molar equivalents with respect to stannous ions). The preparation of the solutions was done without any further protection from air. The content of $Sn^{2+}$ was measured by the usual iodometric titration, with sodium thiosulfate and a known excess of iodine (see example 10), and was carried out in a duplicate over a time interval of 21 days. The solutions were stored at room temperature, in the dark. The development of the concentration of $Sn^{2+}$ (in ppm) in the three solutions over time was according to the following table:

| Time, days | Sol. 1 | Sol. 2 | Sol. 3 |
| --- | --- | --- | --- |
| 0 | 381.0 | 388.5 | 388.2 |
| 0 | 380.5 | 387.1 | 389.0 |
| 8 | 344.4 | 388.5 | 387.0 |
| 8 | 349.1 | 390.7 | 389.0 |
| 15 | 276.4 | 392.8 | 392.7 |
| 15 | 294.7 | 393.1 | 393.0 |
| 21 | 116.5 | 392.2 | 392.7 |
| 21 | 168.0 | 392.4 | 392.2 |

Both solutions 2 and 3 were completely stable within experimental error over 21 days. In contrast thereto, solution 1 was oxidized with a mean rate of about 11 ppm $Sn^{2+}_{aq}$ per day by the oxygen-content of the dissolved air in the aqueous solution. Therefore it can be concluded that one molar equivalent of added nitrate with respect to stannous ions (solution 2) works equally well in stabilising stannous ions as two molar equivalents of nitrate with respect to stannous ions (solution 3). The stoichiometric ratio of nitrate to stannous ions during the observed time interval of about 3 weeks does not seem to have any influence on the stabilization power of the nitrate ions.

Example 14

Stability of Stannous Ion Solutions Under Different Storage Conditions

Three aqueous solutions of 400 ppm intial stannous ion content (ex stannous fluoride) were prepared. The first solution was devoid of nitrate, but the second and third solutions contained 340 ppm nitrate (ex potassium nitrate, 1 molar equivalent nitrate based on stannous ions). Table 1 shows in the secondmost left column the time dependence of the concentration of stannous ions (in ppm) when the first solution was stored without being degassed, and without taking any other measures against oxygen at normal daylight in a transparent bottle. The secondmost right column of table 1 shows the time dependence of the concentration of stannous ions when the second solution was stored without being degassed and without taking any other measures against oxygen at normal daylight in a transparent bottle. The right column of table 1 shows the time dependence of the concentration of stannous ions when the third solution was stored without being degassed and without taking any other measures against oxygen, but in the dark.

TABLE 1

| Elapsed storage time (days) | no nitrate, light | 1 eq. nitrate, light | 1 eq. nitrate, dark |
| --- | --- | --- | --- |
| 0 | 381.24 | 389.2 | 388.91 |
| 14 | 150.16 | 297.23 | 391.45 |
| 21 | 44.74 | 200.83 | 387.50 |

It can be seen that in the first solution the amount of solvated stannous ions decreased over a period of 21 days to about one tenth of the original level (secondmost left column). In the second solution the stannous ion concentration is lowered to half the initial level over a storage period of 21 days (secondmost right column). In the third solution no decrease at all in the concentration of stannous ions was observed over a storage period of 21 days (right column).

Example 15

Stability of Mouthrinses Under Different Storage Conditions

Three mouthrinses similar to the meridol mouthrinse solution marketed by the applicant of the instant invention were prepared (the formulation was similar to the one of instant example 7). The first mouthrinse was devoid of nitrate, but the second and third mouthrinses contained 340 ppm nitrate (ex potassium nitrate, 1 molar equivalent nitrate based on stannous ions). Table 2 shows in the secondmost left column the time dependence of the concentration of stannous ions (in ppm) when the first mouthrinse was stored without being degassed and without taking any other measures against oxygen at normal daylight in a transparent bottle for 21 days. The secondmost right column of table 2 shows the time dependence of the concentration of stannous ions of the second mouthrinse under the same storage conditions. The right column of table 2 shows the time dependence of the concentration of stannous ions when the third mothrinse was stored in the dark, again without taking any precautions against oxygen gas, again over a storage period of 21 days. The values in table 2 are in all cases mean values plus standard deviations from six individual determinations (see example 10).

TABLE 2

| Elapsed storage time (days) | meridol alike no nitrate, light | meridol alike + 1 eq. nitrate, light | meridol alike + 1 eq. nitrate, dark |
| --- | --- | --- | --- |
| 0 | 386.3 ± 2.3 | 386.7 ± 3.4 | 364.5 ± 2.6 |
| 14 | 181.8 ± 10.3 | 288.2 ± 21.4 | 323.0 ± 3.6 |
| 21 | 42.7 ± 8.3 | 223.2 ± 46.3 | 302.8 ± 2.9 |

The behaviour of these three mouthrinses is similar as the behaviour of the three solutions of example 14.

The invention claimed is:

1. An oral care composition comprising
   a) an aqueous phase;
   b) stannous ions solvated in the aqueous phase;
   c) nitrates solvated in the aqueous phase; wherein the total content of said solvated nitrates is such that the molar amount of nitrogen in the aqueous phase, measurable as free nitrate, is 0.1 to 1.8 times the molar amount of solvated stannous ions; and
   d) a flavour substance;
   wherein the aqueous phase comprises 100 to 400 ppm of solvated stannous ions.

2. The oral composition of claim 1, wherein in the aqueous phase the total content of solvated nitrates is such that the molar amount of nitrogen in the aqueous phase, measurable as free nitrate is 1.5 to 0.75 times the molar amount of solvated stannous ions.

3. The oral composition of claim 1, wherein the aqueous phase comprises 150 to 400 ppm of solvated stannous ions.

4. The oral composition of claim 1, wherein the aqueous phase comprises 50 to 2000 ppm of solvated fluoride ions.

5. The oral composition of claim 1, which is a mouthrinse.

6. A single-compartment storage container or single-compartment storage and dispensing container, each comprising the oral care composition of claim 1.

7. The storage container or storage and dispensing single compartment of claim 6, wherein the oral care composition contains solvated oxygen gas.

8. The storage container or storage and dispensing single compartment of claim 6, furthermore comprising a gas phase, wherein the gas is air.

9. A process for storing the oral care composition of claim 1, comprising the steps of
   a) filling the composition of claim 1 into a single compartment storage and dispensing container, wherein
      a1) the composition is not degassed before filling into the container, or
      a2) the container is not purged with inert gas before filling with the composition, or
      a3) the container is not evacuated before filling with the composition, or
      a4) the container is not purged with inert gas after filling with the composition, or
      a5) the container is not evacuated after filling with the composition;
   b) closing the container obtained from a); and
   c) putting the container obtained from b) to storage.

10. The process of claim 9, wherein in step a):
    a1) The composition is not degassed before filling into the container, and
    a2) the container is not purged with inert gas before filling with the composition, and
    a3) the container is not evacuated before filling with the composition, and
    a4) the container is not purged with inert gas after filling with the composition, and
    a5) the container is not evacuated after filling with the composition.

11. An oral care composition comprising
    a) stannous ions;
    b) nitrates wherein the molar ratio of nitrates to stannous ions is 0.1 to 1.8; and
    c) a flavour substance,
    wherein the composition is aqueous, and the stannous ions comprises 100 to 400 ppm.

12. The oral composition of claim 11, wherein the molar ratio of nitrates to stannous ions is 0.75 to 1.5.

13. The oral composition of claim 11, wherein stannous ions comprises 150 to 400 ppm.

14. The oral composition of claim 12, wherein the molar ratio of nitrates to stannous ions is 0.9 to 1.1.

15. The oral composition of claim 14, wherein the aqueous phase comprises 50 to 2000 ppm of solvated fluoride ions.

* * * * *